United States Patent
Godula-Jopek et al.

(10) Patent No.: US 10,663,454 B2
(45) Date of Patent: May 26, 2020

(54) HANDHELD AIR SAMPLER DEVICE, AIR SAMPLING ARRANGEMENT, FILTER MAGAZINE FOR STORING AND PREDEFINED POSITIONING FILTER ELEMENTS ON A BACKING ELEMENT OF A HANDHELD FILTER DEVICE, METHOD FOR APPLYING A FILTER ELEMENT TO A BACKING ELEMENT OF A HANDHELD AIR SAMPLING DEVICE

(71) Applicant: Airbus Defence and Space GmbH, Taufkirchen (DE)

(72) Inventors: Agata Godula-Jopek, Taufkirchen (DE); Ulrich Reidt, Schwalmstadt (DE); Johann Reichenberger, Ainring (DE); Thomas Ziemann, Inning Am Holz (DE); Krzysztof Warmuzinski, Zabrze (PL)

(73) Assignee: Airbus Defence and Space GmbH (DE)

( * ) Notice: Subject to any disclaimer, the term of this patent is extended or adjusted under 35 U.S.C. 154(b) by 241 days.

(21) Appl. No.: 15/831,613

(22) Filed: Dec. 5, 2017

(65) Prior Publication Data

US 2018/0164283 A1 Jun. 14, 2018

(30) Foreign Application Priority Data

Dec. 14, 2016 (EP) ..................................... 16204039

(51) Int. Cl.
*G01N 33/497* (2006.01)
*B01D 46/00* (2006.01)
(Continued)

(52) U.S. Cl.
CPC ............ *G01N 33/497* (2013.01); *A61B 5/082* (2013.01); *A61B 5/097* (2013.01); *A61L 9/20* (2013.01);
(Continued)

(58) Field of Classification Search
CPC .. G01N 33/497; G01N 1/2205; G01N 1/2273; G01N 2001/028;
(Continued)

(56) References Cited

U.S. PATENT DOCUMENTS 5,465,728 A * 11/1995 Phillips .................. A61B 5/097
128/204.17
6,087,183 A * 7/2000 Zaromb ............... G01N 1/2205
422/52
(Continued)

FOREIGN PATENT DOCUMENTS

WO 2007/130522 A2 11/2007

OTHER PUBLICATIONS

EP 16204039.8 Search Report dated Feb. 20, 2017.

*Primary Examiner* — Nathaniel T Woodward
(74) *Attorney, Agent, or Firm* — Lerner, David, Littenberg, Krumholz & Mentlik, LLP

(57) ABSTRACT

A handheld air sampler device for enrichment of airborne substances and/or particles, in particular microorganisms, includes: an inlet configured for air intake into a flow channel; an outlet configured for fluidic ally connecting the flow channel to an external vacuum device; a permeable backing element arranged in the flow channel, the backing element being configured to receive and support a filter element; and a sealing element configured for sealing a filter element received on the backing element such that, when a negative pressure is applied to the outlet, air entering the inlet forms an airstream passing the filter element and (Continued)

airborne substances and/or particles, in particular microorganisms, are enriched in the filter element. An air sampling arrangement includes a handheld air sampler device of this type.

25 Claims, 12 Drawing Sheets

(51) Int. Cl.
    *A61B 5/097*     (2006.01)
    *A61B 5/08*     (2006.01)
    *G01N 1/22*     (2006.01)
    *A61L 9/20*     (2006.01)
    *G01N 1/02*     (2006.01)

(52) U.S. Cl.
    CPC ..... *B01D 46/0005* (2013.01); *B01D 46/0041* (2013.01); *G01N 1/2205* (2013.01); *G01N 1/2273* (2013.01); *A61L 2209/12* (2013.01); *A61L 2209/14* (2013.01); *G01N 2001/028* (2013.01); *G01N 2001/2244* (2013.01); *G01N 2001/2288* (2013.01)

(58) Field of Classification Search
    CPC .... G01N 2001/2244; G01N 2001/2288; A61L 9/20; A61L 2209/12; A61L 2209/14; A61B 5/082; A61B 5/097; B01D 46/0005; B01D 46/0041
    USPC .......................................................... 73/863
    See application file for complete search history.

(56) References Cited

U.S. PATENT DOCUMENTS

| | | | | |
|---|---|---|---|---|
| 6,138,521 | A * | 10/2000 | Basch | G01N 1/2273 73/863.25 |
| 6,248,078 | B1 * | 6/2001 | Risby | A61B 5/097 600/529 |
| 7,122,065 | B2 * | 10/2006 | Fox | G01N 1/24 55/306 |
| 7,472,612 | B2 * | 1/2009 | Zaromb | G01N 1/2214 73/31.01 |
| 9,169,521 | B1 * | 10/2015 | Rajagopal | B01L 3/5027 |
| 2005/0137491 | A1 * | 6/2005 | Paz | A61B 5/087 600/543 |
| 2007/0068284 | A1 * | 3/2007 | Castro | G01N 1/2205 73/863.21 |
| 2009/0268201 | A1 * | 10/2009 | Call | G01N 15/0625 356/338 |
| 2016/0022946 | A1 * | 1/2016 | Sislian | G01N 1/2202 600/543 |

* cited by examiner

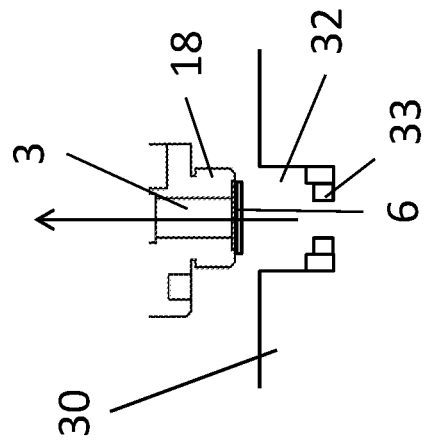
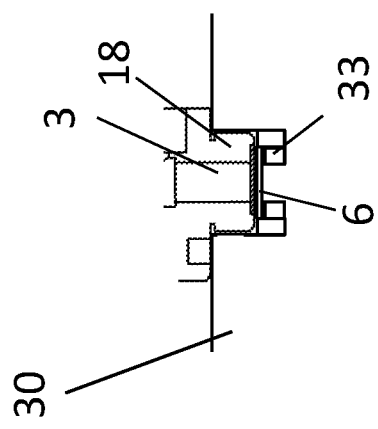
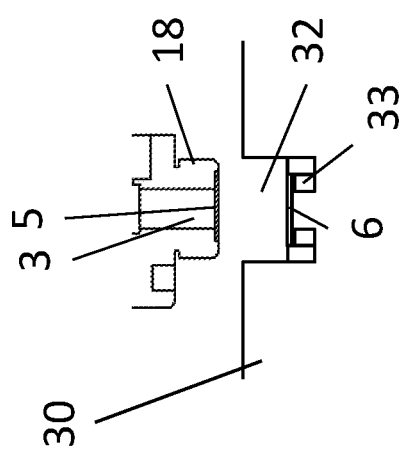

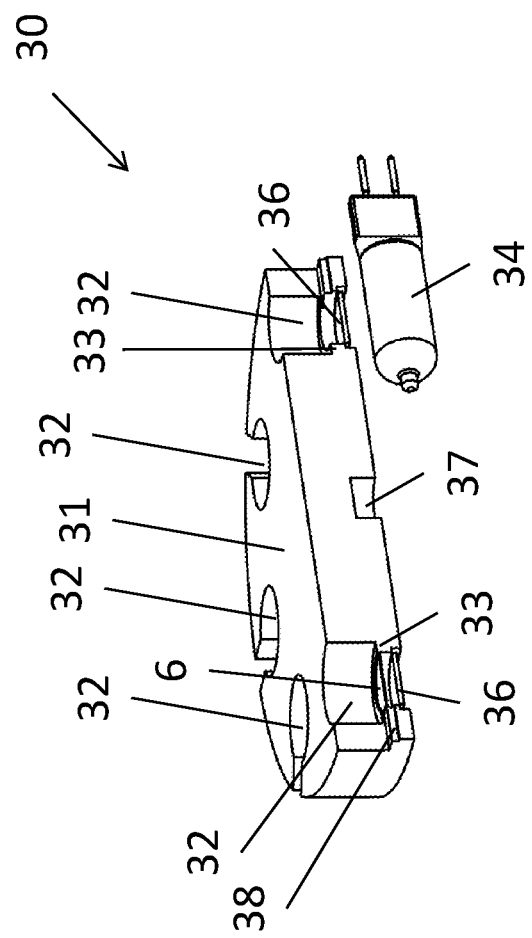

HANDHELD AIR SAMPLER DEVICE, AIR SAMPLING ARRANGEMENT, FILTER MAGAZINE FOR STORING AND PREDEFINED POSITIONING FILTER ELEMENTS ON A BACKING ELEMENT OF A HANDHELD FILTER DEVICE, METHOD FOR APPLYING A FILTER ELEMENT TO A BACKING ELEMENT OF A HANDHELD AIR SAMPLING DEVICE

FIELD OF THE INVENTION

The present invention pertains to a handheld air sampler device, an air sampling arrangement, a filter magazine for storing and predefined positioning filter elements on a backing element of a handheld filter device of this type and a method for applying a filter element to a backing element of a handheld air sampling device of this type.

Although applicable to any kind of air sampling filter, the present invention and the problem on which it is based will be explained in greater detail with reference to air sampling devices using gelatin filters.

BACKGROUND OF THE INVENTION

Airborne bacterial, viral and fungal cells and spores may be present in the air as bioaerosols (in droplets), which are very small individual particles that stay suspended in air for long periods or may aggregate as larger clumps that settle rapidly onto surfaces. It is desirable to identify airborne pathogens, for example to prevent an outbreak of diseases. However, detecting airborne pathogens is challenging due to the comparably low density of pathogens in the air.

There are generally two principle ways of monitoring the microbiological population of the air, passive monitoring and active sampling. Passive monitoring is usually done using so called settle plates, which are often standard Petri dishes containing appropriate culture media. These are opened and exposed to the air for a predetermined time and then incubated to allow visible colonies to develop and be counted. The active air sampling, in contrast, comprises an active enrichment step. Thereby, a known volume of air is physically drawn on or through a particle collection device, the so called air sampler.

There are different types of air samplers. For example, two very common and most commercially available types of air samplers are, the so called impingers, which use a liquid medium for particle collection, and the so called impactor samplers, which use a solid or adhesive medium, such as standard agar plates, for particle collection. For example, a laminar air flow can be directed onto the collection surface of an impactor.

Another method of active air sampling is filtering the sample, whereby air is drawn by a pump or other vacuum device through a membrane filter. An advantageous kind of membrane filters for this purpose are gelatin membrane filters. Due to the possibility to dissolve the gelatin filters, microorganisms can be recovered and transferred to a detection assay. Gelatin membrane filters are usually used in stationary air samplers. One kind of air sampler known by the applicant is configured for air monitoring and constructed as a stationary system. Other kinds of air samplers known by the applicant include a battery, a vacuum pump, a control panel and a filter head together in one housing and are configured portable.

BRIEF SUMMARY OF THE INVENTION

It is one of the ideas of the present invention to provide for an improved air sampler concept.

A handheld air sampler device is provided for enrichment of airborne substances and/or particles, in particular microorganisms, comprising: an inlet configured for air intake into a flow channel; an outlet configured for fluidically connecting the flow channel to an external vacuum device; a permeable backing element arranged in the flow channel, the backing element being configured to receive and support a filter element; and a sealing element configured for sealing a filter element received on the backing element such that, when a negative pressure is applied to the outlet, air entering the inlet forms an airstream passing the filter element and airborne substances and/or particles, in particular microorganisms, are enriched in the filter element.

Furthermore, an air sampling arrangement is provided, comprising: a handheld air sampler device according to the invention; a separate vacuum device fluidically connected to the outlet of the handheld air sampler device; a filter element received between the backing element and the sealing element of the handheld air sampler device such that a negative pressure applied to the outlet generates an airflow through the inlet which entirely passes the filter element for enrichment of airborne substances and/or particles, in particular microorganisms.

Furthermore, a filter magazine is provided for storing and predefined positioning filter elements on a backing element of a handheld air sampler device according to the invention, the filter magazine comprising: a top plate comprising a recess, in particular a recess dimensioned equal to a flange of the handheld air sampler device, such that the recess fits with a holding portion of the handheld air sampler device; a filter receiving protrusion or step arranged in the recess for holding a filter element in a predefined position such that the filter element can be received on the backing element of the handheld air sampler device in a predefined position by inserting the backing element, in particular together with the holding portion of the handheld air sampler device, into the recess.

Furthermore, a method for applying a filter element to a backing element of a handheld air sampling device according to the invention is provided, the method comprising the following steps: interrupting airflow in the flow channel; inserting the backing element into a recess of a top plate of a filter magazine according to the invention with a filter element stored therein; and continuing airflow in the flow channel such that a pressure difference and a resulting force for holding the filter element on the backing element is generated.

One idea of the present invention is to provide for an handheld air sampler device working with a filtration principle and being externally supplied with vacuum via its outlet. Thereby, the device is small and lightweight since any vacuum supply related components are external. Thus, the device is modular and easy to use and flexibly adaptable to different applications.

In particular, the device according to an embodiment of the invention is configured for the use of gelatin membrane filters. Especially, the backing element provides support for the gelatin membrane filter to mechanically withstand pressure differences and resulting forces caused by the fluidic resistance of the gelatin membrane when a negative pressure, in particular vacuum, is applied.

A gelatine membrane filter is usually used in comparably big filter heads, the comparably big size of which usually is a measure to not expose the membrane to high pressure differences. According to an embodiment of the present invention, however, a gelatin membrane filter or other kind of filter can be used in a comparably small sectional area of the flow channel, in combination with relatively high flow rates which allows both, a compact handheld design of the device and fast enrichment.

A filter element used according to an embodiment of the invention is configured for sampling airborne microorganisms, in particular including viruses, especially pathogens, and may have any suitable configuration for this purpose. Especially, a gelatin membrane filter may be used, which provides the opportunity to, apart from bacteria and fungi, detect also viruses which due to the very small size of viruses usually can hardly be detected with other kinds of filters.

According to one aspect of the invention, detecting microorganisms including viruses is now possible with a light-weight and small handheld air sampling device, in particular in new applications such as respiratory or surface air sampling. In this way, the invention provides an apparatus which, in addition to the classic room air sampling, is also configured also for air sampling of surfaces or breath, and can be easily adapted therefore.

For example, for medical applications the inlet may comprise a mouthpiece-like nozzle and patients can blow their breath at the gelatin membrane by a moderate negative pressure and flow rate applied to the outlet, for example by means of a moderate pumping rate of a vacuum pump. Accordingly, an embodiment of the invention can be used in a specific application for the detection of respiratory diseases.

For surface sampling, which is another specific application enabled by the handheld design of the handheld air sampler device, an optimized wiping nozzle can be used. The wiping nozzle together with the handheld design of the device allows easy wiping of a surface during the sampling, in particular a predetermined surface area such as for example a standard area of 1 m$^2$, for example in a standardized wiping pattern. In this way, all kinds of surfaces, also special kinds of surfaces such as e. g. skin, can be tested by air sampling.

The device can also be used with or without a nozzle for classic air sampling of room or indoor (inside) air or outdoor (outside) air.

Other applications, such as e.g. sampling of organic or inorganic substances, such as toxins, explosives, drugs or the like, are possible.

For example, the backing element extends over the whole cross section of the flow channel. According to an advantageous embodiment, the backing element is configured as a sieve arranged in the flow channel between the inlet and the outlet.

The handheld air sampler device itself is in particular a pumpless device configured to be connected to an external vacuum device, in particular a stationary vacuum device or pump (which is not handheld). Therefore, the outlet for example comprises a connecting means for connection to a vacuum tube such that a negative pressure (underpressure), in particular a vacuum, generated by the external vacuum device can be applied at the outlet.

With an air sampling arrangement according to an embodiment of the invention, the handheld air sampling device can be used for sampling air. Subsequently, the filter element may be removed for analysis.

For example, the outlet of the device is removably connected to the vacuum device. Accordingly, the device can be used as a module with any suitable vacuum device. In particular, a standard vacuum pump or other type of vacuum supply, in particular suitable also for other applications, can be used for sampling.

With a filter element of the arrangement inserted in the flow channel and received on the backing element, airborne substances and/or particles, in particular microorganisms, can be enriched.

With various nozzles, various special applications of the arrangement, such as enrichment of respiratory microorganisms or surface sampling, are possible. Of course, also classic air sampling of indoor or outdoor air is possible.

The filter element is usually used for one predefined sampling step or sampling cycle only and removed or replaced afterwards. During the sampling, the filter element is for example sealed by the sealing element in such a way that air passing the flow channel may not bypass the filter element. In this way, a defined volume of sampled air can be predetermined for or determined from a flow rate, which is controlled by the vacuum device, and the duration of the sampling, in particular a sampling step or a sampling cycle.

The filter element is not particularly restricted or limited. According to an embodiment, the filter element may be a suitable filter, for example at least one of a group consisting of gelatin filter, gelatin membrane filter, cellulose filter, nitro cellulose filter, nylon filter, nano-cellulose filter, polyvinylidene difluoride membrane filter, polytetrafluoroethylene membrane filter, polyethersulfone membrane filter, MEMS filter (etched disk), and combinations thereof.

The filter element fits on/with the backing element, and in some embodiments spans the cross-section of the flow channel. The sealing element outwardly fits on/with the filter element and provides a passage for the airstream, which thus may entirely pass the outwardly sealed filter element with no bypass.

The form of the flow channel and/or the backing element and/or the filter element may be any suitable form and is not particularly restricted. For example, the cross section of the flow channel and/or the backing element and/or the filter element may be formed circular. Other possible forms of the cross section and/or the backing element and/or the filter element may be oval, triangular, square or the like.

Owing to the handheld design, the diameter of the flow channel is, compared to known air samplers, relatively small. For example, the diameter may be in the range of 4 mm to 12 mm, in particular 6 mm to 10 mm, in some embodiments 8 mm. The filter may have, for example, a diameter in the range of 8 mm to 20 mm, in particular 10 mm to 15 mm, in some embodiments 13 mm.

For example, the filter element may be configured as cut out from commercially available gelatin membrane filters (which usually have a much bigger dimension, in particular diameter).

The filter magazine allows quick, precise and sterilized placement or replacement of filter elements on the backing element.

The placement or replacement in particular can be carried out by the method for applying a filter element to a backing element of a handheld air sampling according to an aspect of the invention.

Thereby, the airflow can be interrupted in particular by closing a valve of the handheld air sampling device. Accordingly, the airflow can be continued again by opening the valve of the handheld air sampling device.

Inserting the backing element into a recess of a top plate of a filter magazine may comprise inserting the holding portion of the handheld air sampling device. The holding portion may be formed, for example, as a pipe end with the backing element spanning the inner cross section of the pipe end at the edge thereof. Accordingly, the backing element is arranged on the lower end and thus gets into contact with the filter element when the holding portion is inserted into the recess.

Before inserting the backing element into the recess, any used filter (if any) is removed from the backing element.

The method may further comprise removing the backing element, in particular together with the holding portion, from the recess after or while continuing the airflow. Thus, the filter element is held on the backing element in the predefined position during the removing of the backing element by means of the airflow.

Furthermore, the method may comprise removing the inlet before the backing element is inserted into the recess. Optionally or in addition, the method may comprise reattaching the inlet after removing the backing element from the recess. In particular, removing the inlet may comprise detaching a flange thereof from a holding portion of the handheld air sampler device, in particular by detaching a magnetic holder. Reattaching the inlet may comprise attaching the flange to the holding portion, in particular by attaching a magnetic holder.

As a magnetic holder, for example, a permanent magnet may be attached to or integrated in the holding portion and/or attached to or integrated in the flange. The permanent magnet is configured for attaching the flange to the holding portion.

According to an embodiment of the handheld air sampler device, the inlet and/or the outlet is at least partially formed as a handhold portion. Accordingly, the inlet and/or the outlet is, for example, formed with a long and slim shape. Alternatively or in addition, the outlet is at least partially formed integrated with or directly connected to a handhold portion. For example a tube like grip material or a grip shaped housing may surround the inlet and/or outlet. In this way, the device can be conveniently handheld in use, in particular with one hand only.

According to an embodiment, the inlet and the outlet are configured removable from each other for inserting, removing or replacing the filter element. Thereby, additional portions or elements of the device may be arranged between the inlet and the outlet. In this way, by removing the inlet and the outlet from each other, the filter element can be easily accessed and replaced, inserted or removed.

According to an embodiment, a valve is arranged in the flow channel for controlling an airflow through the flow channel. In particular, the valve comprises an operating element. In some embodiments, the operating element is positioned hand operable in use, especially one-handed operable with the same hand the device is handheld with. In this way, easy and convenient control of the airflow with only one hand is enabled. In particular, the valve is configured and arranged to control the airflow at the inlet with no delay. Thus, airflow control is faster and more precise than by controlling a negative pressure of the vacuum device, for example by controlling the pump speed of a vacuum pump. Accordingly, a very exact control of the airflow, in particular when inserting, removing or replacing the filter element, is possible. Furthermore, the precise control of the airflow also enables new applications of air sampling, for example locally concentrated air sampling, air sampling with short duration, air sampling on specific areas of a surface, or the like.

According to an embodiment, the valve is arranged in the flow channel between the inlet and the outlet. For example, the valve may comprise a button configured to allow an airflow when the button is released and to interrupt the airflow when the button is pressed. In this way, the sampling can be stopped by pressing the button, for example in order to exchange or replace filter elements. In particular embodiments, the button may mechanically act on the valve, especially a piston thereof, to close it when the button is pushed. A spring may be provided to revert the piston and the button to an open position, when the button is released. According to other embodiments, the valve may comprise an electronic control and an actor coupled with it such that the operating element is configured to input control commands.

According to an embodiment a flow direction through the inlet is at an angle to a flow direction through the outlet. For example, the angle may be a right angle such that the directions are perpendicular to each other. In particular, the angled arrangement of the inlet and the outlet may be realized by the valve and/or holding portion having connections to the inlet and/or outlet directed in different directions.

In an embodiment, the button for controlling the valve is positioned next to or integrated with a handhold portion, which may be formed with the inlet or outlet. In this way, the device can be advantageously controlled one-handed.

According to an embodiment, the inlet is provided with a nozzle configured as mouthpiece for sampling of breath to enrich respiratory microorganisms in the filter element. In this way, the device can be used in a respiratory application. In particular, the nozzle may be attached to the inlet by sliding it positively onto the inlet. Thus, an adaption of the device by attaching the nozzle configured as mouthpiece to the inlet for a respiratory application is easy, fast and removable. According to other embodiments, the inlet may be formed integral with the nozzle configured as mouthpiece. In this case, an inlet without nozzle may be replaced by the inlet formed integral with the nozzle for adaption.

According to another embodiment, the inlet is provided with a surface vacuum nozzle configured for wiping a surface area. In some embodiments, the inlet may be formed integral with the surface vacuum nozzle. In this case, an inlet without nozzle may be replaced by the inlet formed integral with the nozzle for adaption. Alternatively, a surface vacuum nozzle may be configured to be attached to the inlet.

In some embodiments, the surface vacuum nozzle comprises a nozzle surface with a plurality of open channels to avoid stucking on the surface area when a negative pressure is applied. In this way, for sampling, easy and convenient wiping of a surface with the device is possible, in particular with the nozzle surface and the surface area being in contact, when a vacuum is applied to the outlet.

According to some embodiments, the filter element is configured insertable between the backing element and the sealing element. In this way, the filter element can be sealed, in particular fully circumferentially sealed, in the flow channel. Accordingly, bypassing of the filter element is prevented and accuracy of the results of the sampling is ensured. In particular, inserting the filter element between the backing element and the sealing element is realized by sealedly clamping the filter element between the backing element and the sealing element. Accordingly, all airflow passing the flow channel (the entire airstream) passes the filter element.

According to some embodiments, the handheld air sampler device comprises a holding portion at least partially forming the flow channel, wherein the inlet comprises a flange removably attachable to the holding portion with the sealing element therebetween such that the filter element can be sealedly clamped between the backing element and the sealing element when the flange is attached. The backing element is for example attached to the holding portion, in particular at the edge thereof. For holding the flange on the holding portion, the inlet can be removably attachable by means of a fastener or holder. In particular, the flange is removably attachable to the holding portion with a magnetic holder integrated in the holding portion and/or the flange. A passage opening of the flange is in some embodiments smaller in cross-section or diameter compared to the filter and/or compared to the sealing element. A receiving section of the flange is formed such that the sealing element and the filter element can be received between the backing element and the receiving section in a defined position.

According to an embodiment of the filter magazine, the recess is configured as a through hole and a first sterilizing means is arranged underneath the top plate for sterilizing a filter stored in the recess. In particular, the sterilizing means is positionable in alignment with the recess configured as through hole. In this way, a filter element stored in the recess may be sterilized by the sterilizing means from underneath. The sterilizing means may be configured for example as a separate sterilizing device or as an integrated sterilizing element. It may work for example based on UV-, heat- or chemical sterilization or a combination thereof.

According to an embodiment, the top plate is formed as a revolver like wheel which can be turned around its center.

Furthermore, according to an embodiment, a plurality of recesses are provided in the top plate.

The recesses are for example evenly distributed and concentrically arranged on the revolver like wheel. The sterilizing means is accordingly positioned in a corresponding distance to the center of the wheel. In this way, a filter element received in any of the recesses can be sterilized by turning the wheel to the position of the sterilizing means. Furthermore, the backing element can be sterilized by inserting it into a recess in alignment with the sterilizing means, if no filter element is stored in the recess. In particular, a sterilization of both, the backing element and the filter element may take place in two different recesses.

According to an embodiment, a second sterilizing means is provided underneath the top plate for sterilizing the backing element before a filter is received thereon. Thus, although the working principle is generally equal to the embodiment with one sterilizing means, the top plate or wheel advantageously can stay in one position and both, the backing element and the filter element can be sterilized at the same time. Therefore, the backing element of the device can be first inserted into a recess situated at or above, in particular in alignment with, the second sterilizing means for sterilizing the backing element and afterwards inserted into a recess situated at or above, in particular in alignment with, the first sterilizing means for applying the filter element to the backing element. In this way, contamination of the backing element and of the filter before sampling is reliably avoided.

According to yet another embodiment, the first and/or second sterilizing means comprises a UV lamp. In this case, in particular a UV transmitting window is attached to the lower side of the top plate such that UV light emitted by the UV lamp reaches the filter element through the window. The UV transmitting window may in particular comprise borosilicate and/or sapphire glass. In this way, no contaminations may access the recesses from underneath and the filter elements can be stored in the recesses also for longer times.

According to an embodiment, the recess may have a venting bore or channel entering the recess between the filter receiving protrusion or step and the UV transmitting window allowing an airflow through the recess if an underpressure is applied. In this way, continuing airflow in the flow channel when the backing element is inserted in the recess generates a pressure difference at the filter element and a resulting force for holding the filter element on the backing element. Accordingly. the filter element is held on the backing element of the handheld filter device in its pre-defined position, when the backing element is removed again from the recess.

The invention will be explained in greater detail with reference to exemplary embodiments depicted in the drawings as appended.

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as they become better understood by reference to the following detailed description. The elements of the drawings are not necessarily to scale relative to each other. In the figures, like reference numerals denote like or functionally like components, unless indicated otherwise.

BRIEF DESCRIPTION OF THE DRAWINGS

FIG. 9A-9C schematically illustrate steps of a method for applying a filter element to a backing element of a handheld air sampling device according to an embodiment.

FIG. 10 schematically illustrates a filter magazine in a sectional perspective view.

Although specific embodiments are illustrated and described herein, it will be appreciated by those of ordinary skill in the art that a variety of alternate and/or equivalent implementations may be substituted for the specific embodiments shown and described without departing from the scope of the present invention. Generally, this application is intended to cover any adaptations or variations of the specific embodiments discussed herein.

DETAILED DESCRIPTION

Figure 1:
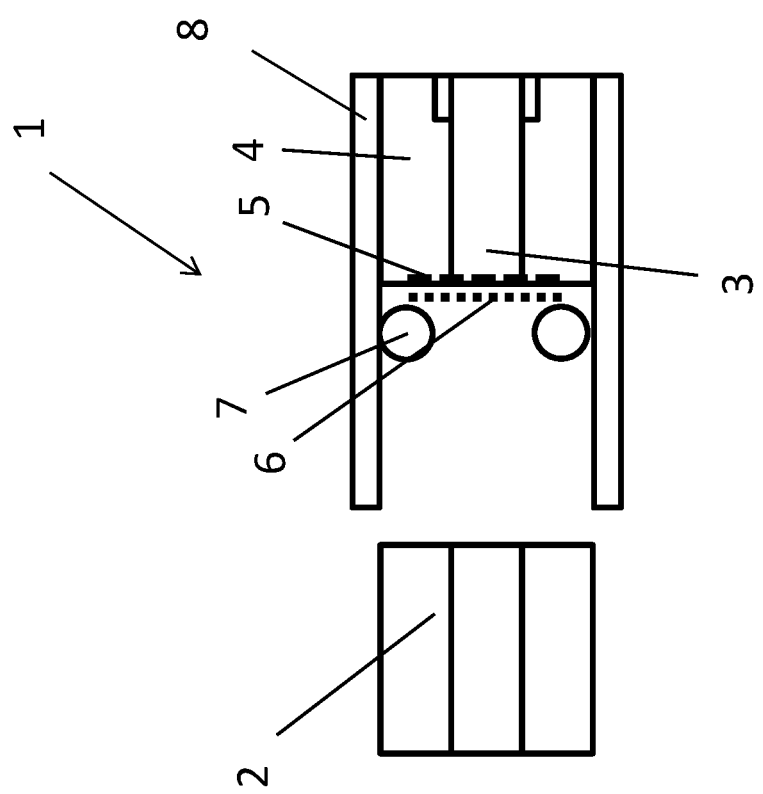
FIG. 1 schematically illustrates a handheld air sampler device according to an embodiment in a sectional exploded view.

FIG. 1 schematically illustrates of a handheld air sampler device 1 according to an embodiment in a sectional view.

This embodiment is depicted in the form of a block drawing in order to explain general functions of the handheld air sampler device 1. The structure of the device shown in the block drawing symbolizes components thereof and is not particularly restrictive or limiting. FIG. 1 shows the handheld air sampler device 1 in a pre-mounted state.

The handheld air sampler device 1 comprises an inlet 2 and an outlet 4. Both, the inlet 2 and the outlet 4 are symbolically represented by a block with a central passage forming a flow path 3. The outlet 4 is configured for fluidically connecting the flow channel 3 to an external vacuum device. The inlet is configured for air intake into the flow channel 3. Furthermore, the inlet and the outlet are configured to be removably attached to each other.

The outlet 4 is provided with a handhold portion 8. In this exemplary embodiment, the handhold portion 8 is also configured to allow attachment of the inlet 2.

Within the flow channel 3, a permeable backing element 5 schematically depicted with a dashed line is arranged. The backing element 5 may be configured permeable, for example as a sieve or grid spanning the cross-section of the flow channel 3 and having a plurality of openings, such that it provides sufficient permeability to let an airflow pass through. Furthermore, the backing element 5 is configured to receive and mechanically support a filter element 6 within the flow channel 3, which filter element 6 is schematically depicted in FIG. 1 with a dotted line.

In order to keep the filter element 6 in a predefined position and to seal the filter element 6 to avoid any bypassing of air, a sealing element 7 is arranged between the backing element 5 and the inlet 2. The sealing element 7 is configured for sealing a filter element 6 received on the backing element 5 within the flow channel 3.

Figure 2:
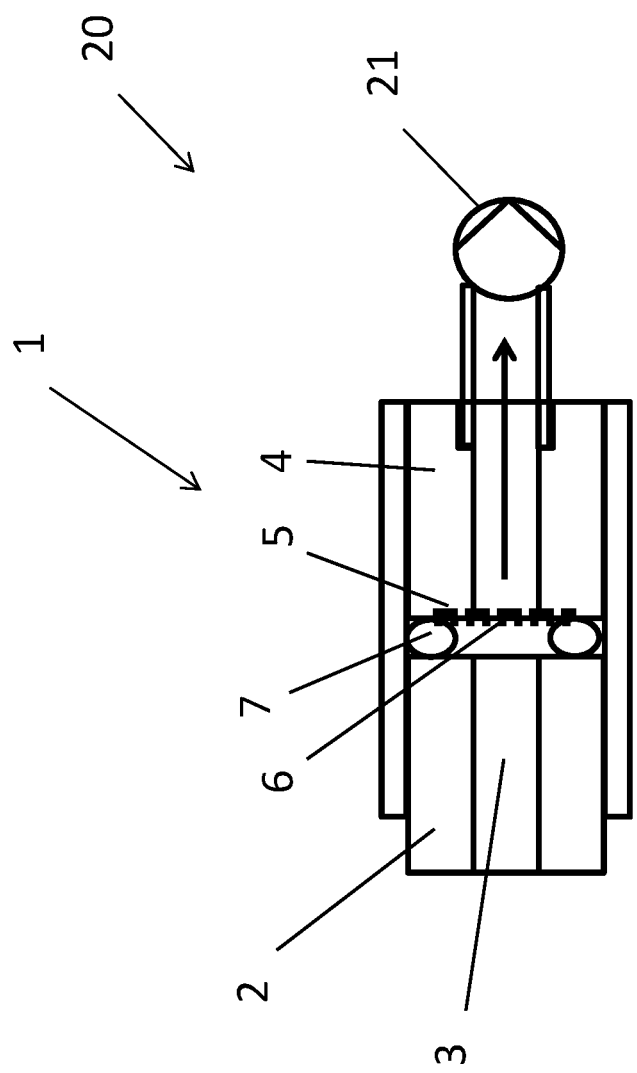
FIG. 2 shows an air sampling arrangement comprising the handheld air sampler device depicted in FIG. 1.

FIG. 2 shows an air sampling arrangement 20 comprising the handheld air sampler device 1 depicted in FIG. 1.

In addition to the handheld air sampler device 1, the air sampling arrangement 20 comprises a vacuum device 21 which supplies the outlet for with a negative pressure or vacuum.

The handheld air sampling device 1 is now shown in a mounted state and the inlet 2 and the outlet 4 are attached to each other. Furthermore, a filter element 6 is sealedly clamped between the backing element 5 and the sealing element 7. A clamping force pressing the sealing element against the backing element is provided by attachment of the inlet 2 and the outlet 4 with each other. In this way, air bypassing the filter element 6 is omitted such that all air passing the flow channel 3 due to the negative pressure applied by the vacuum device 21 passes the filter element 6. Accordingly, when a negative pressure is applied to the outlet 4, an air flow entering the inlet 2 forms an airstream through the flow channel 3 passing the filter element. Thereby, airborne substances and/or particles are enriched in the filter element 6.

In this way, airborne microorganisms can be sampled with the air sampling arrangement 20.

Figure 3:
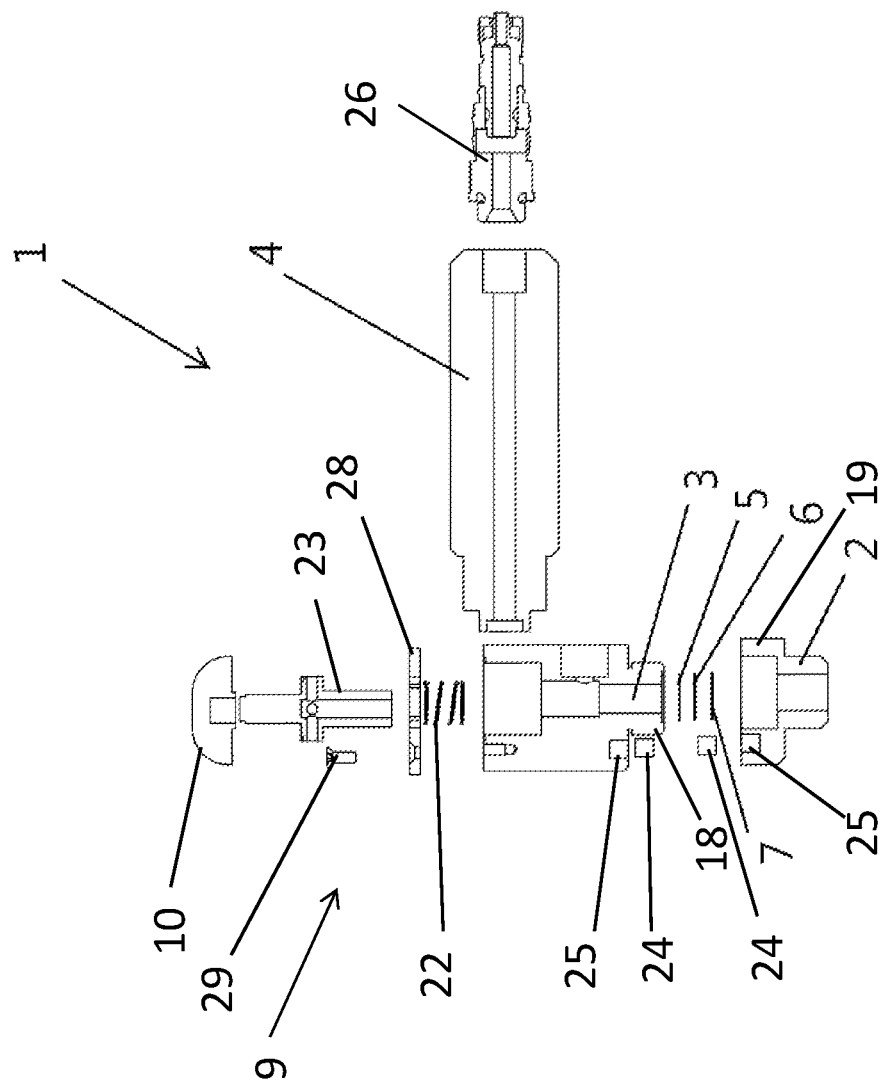
FIG. 3 schematically illustrates a handheld air sampler device according to another embodiment in a sectional exploded view.

FIG. 3 schematically illustrates a handheld air sampler device 1 according to another embodiment in a sectional exploded view.

This embodiment also comprises an inlet 2, an outlet 4, a backing element 5 and a sealing element 7 arranged in a flow channel 3 and a filter element 6 inserted between the backing element 5 and the sealing element 7 and sealedly clamped between them. Although these elements, owing to additional functionality and optimised handheld design, have a different shape, their general function described with reference to FIGS. 1 and 2 can be transferred. Accordingly, only additional or different features will be described in detail.

In this embodiment, as a major difference, additionally a valve 9 is arranged in the flow channel 3 for controlling an airflow. Furthermore, the handheld air sampling device one is provided with a holding portion 18 forming the flow channel 3.

The valve 9 comprises an operating element 10 configured as a button, a spring 22, and the piston 23. The holding portion 18 in an upper section thereof is configured to accommodate the valve 9. In particular, for mounting the valve, the piston 23 and the spring 22 are inserted in the holding portion and held therein by means of a mounting plate 28 and fixation means 29.

In a lower section, the holding portion 18 is configured to accommodate the backing element 5 and to be attached with the inlet 2. For attachment with the inlet, a magnetic holder realized by means of a permanent magnet 24 is integrated in each one of the holding portion 18 and the inlet 2. Therefore, a recess 25 is provided in the holding portion 18 and the inlet 2, respectively.

The inlet 2 is formed with a flange 19 having a receiving portion configured to clamp the filter element 6 between the backing element 5 and the sealing element 7. A passage opening of the flange 19 is for example smaller in diameter compared to the diameter of the filter element 6 and/or compared to the diameter of the sealing element 7.

A side section of the holding portion 18 is configured to be attached and fluidically connected with the outlet 4. For example, the side section of the holding portion may be provided with an internal thread and the outlet with an external thread (not shown).

On its other side, the outlet is configured to be attached with a tube connector 26. In particular, the outlet comprises an internal thread and the tube connector an external thread (not shown).

Figure 4:
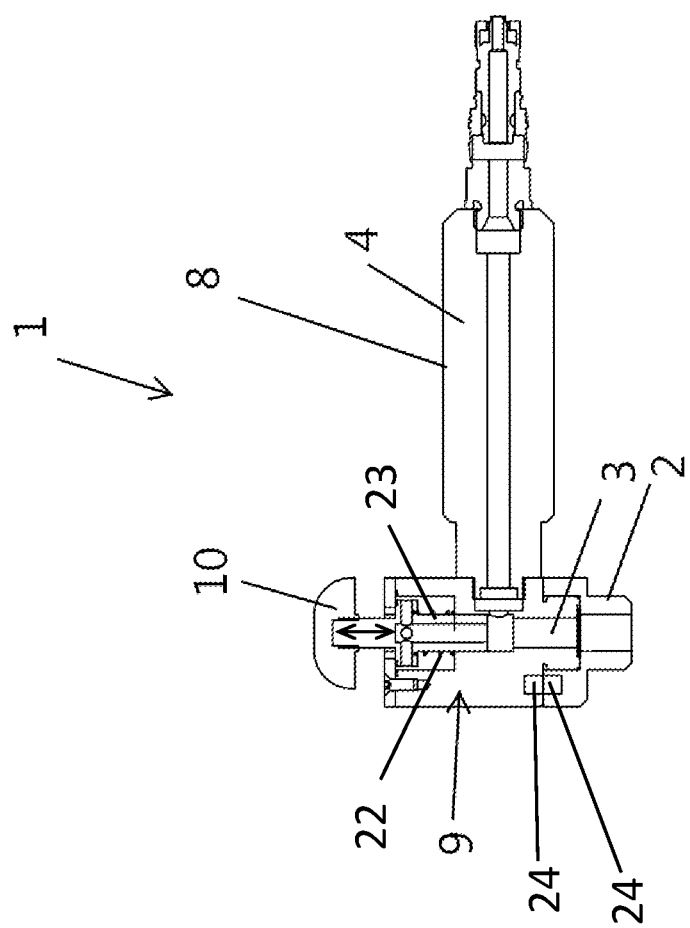
FIG. 4 schematically illustrates the handheld air sampler device depicted in FIG. 3 in a mounted sectional view.

FIG. 4 schematically illustrates the handheld air sampler device 1 depicted in FIG. 3 in a mounted sectional view.

As can be seen from FIG. 4, the piston and the spring are arranged such that the flow channel 3 is open such that an airflow from the inlet 2 to the outlet 4 is possible, in a regular state as shown in FIG. 4 when the operating element 10 is released.

The flow channel 3 is closed in a state when the operating element 10 is operated, here when the button is pressed as indicated with the double arrow in FIG. 4. The piston 23 then closes the fluidic connection between the inlet 2 and the outlet 4 such that an airflow is interrupted.

Furthermore, the spring 22 is configured to revert the piston 23 to the regular state and thus re-open the fluidic connection when the operating element 10 is released again. Therefore, an airflow through the flow channel 3 can be controlled by the valve 9, which is operated via the operating element 10 (by pressing the button).

In the present embodiment, the outlet 4 is formed integrally with a handhold portion 8. Therefore, the device 1 can be handheld and the operating element 10 operated one-handed. In particular, the button can be ergonomically and conveniently pushed with a thumb of a hand the handhold portion 8 is held with.

Figure 5:
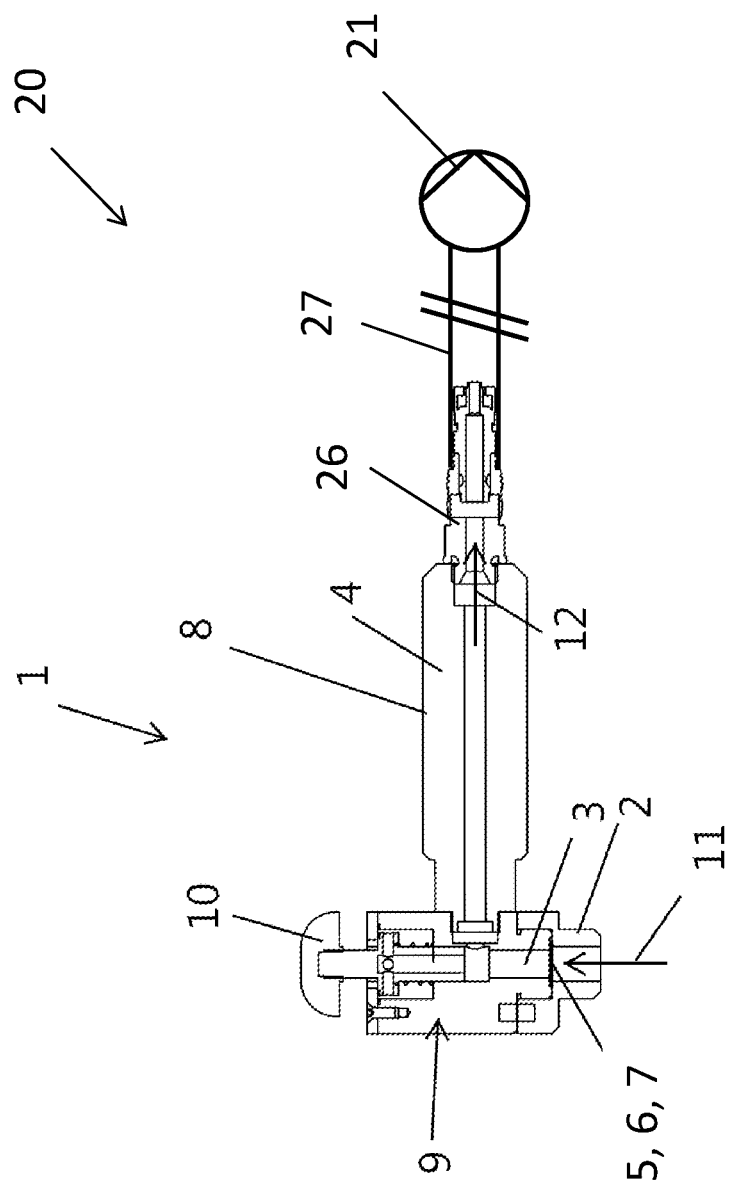
FIG. 5 schematically illustrates an air sampling arrangement comprising the handheld air sampler device depicted in FIG. 4.

FIG. 5 schematically illustrates an air sampling arrangement 20 comprising the handheld air sampler device 1 depicted in FIG. 4.

Similar to the embodiment of FIG. 2, the air sampling arrangement 20 in addition to the handheld air sampler device 1 comprises a vacuum device 21 supplying the outlet 4 with a negative pressure or vacuum.

In the present embodiment, a tube connector 26 and a vacuum tube 27 are provided to fluidically connect the outlet 4 to the vacuum device 21. The vacuum tube 27 can have any suitable form or length for the intended application of the handheld air sampler device, as symbolized by the two parallel lines crossing the vacuum tube 27.

Due to the perpendicular arrangement of the inlet 2 and the outlet 4, a flow direction 11 through the inlet 2 is also perpendicular to the flow direction 12 through the outlet 4. In the present embodiment, the flow direction 11 through the inlet 2 is parallel to the piston 23 and the flow direction 12 through the outlet 4 is radial to the piston 23.

In the configuration depicted in FIG. 5, the air sampling arrangement may for example be used for classic air sampling from the environment indoor or outdoor. For example, a vacuum device, such as a vacuum pump, can be programmed accordingly for automatic sample processing of a predetermined air quantity or volume.

Figure 6:
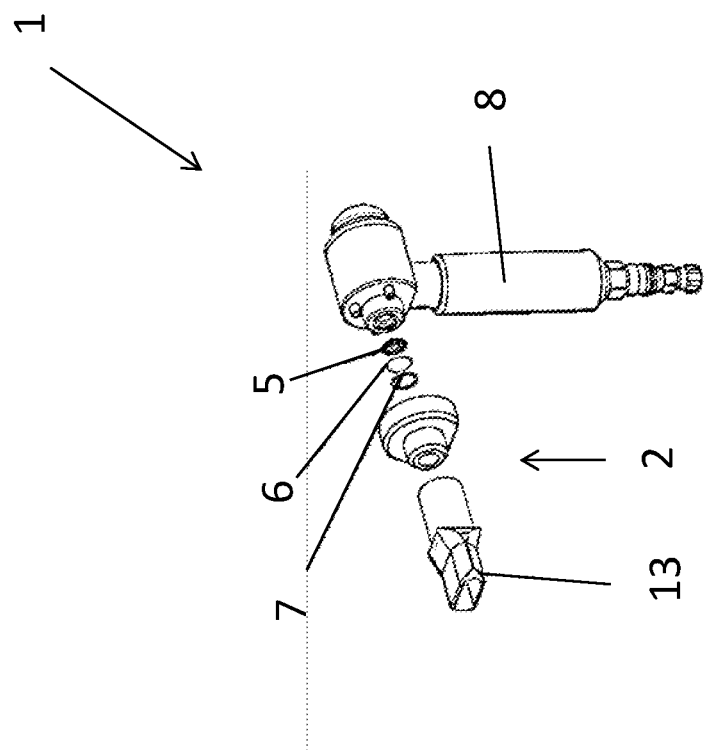
FIG. 6 schematically illustrates a handheld air sampler device according to another embodiment for respiratory sampling application in a perspective exploded view.

FIG. 6 schematically illustrates a handheld air sampler device 1 according to another embodiment for respiratory sampling application in a perspective exploded view.

This embodiment differs from the embodiment of FIG. 5 in that the inlet 2 is provided with a nozzle 13 configured as mouthpiece for sampling of breath to enrich microorganisms, e. g. respiratory microorganisms in the filter element 6. In this way, the device can be used in a respiratory application. The nozzle 13 is formed and configured to be attached to the inlet 2 by sliding it positively onto the inlet 2.

For example, the following respiratory pathogens can be targeted and captured with the sampling device in combination with a suitable filter, e. g. a gelatin filter, the filter being not particularly restricted or limited:

Influenza virus type A & B
Respiratory Syncytial Virus type A & B
Parainfluenza type 1, 2, 3 & 4
Coronavirus type OC43, 229E,
Coronavirus type NL63, HKU1
Rhinovirus
Adenovirus
Human Metapneumovirus
Human Boca virus
*Chlamydophila pneumoniae*
*Mycoplasma pneumoniae*
*Legionella pneumophila*
*Bordetella pertussis*
*Coxiella burnetti*
*Streptococcus pneumoniae*
*Staphylococcus aureus*
Heamophilus influenzae
*Moraxella catarrhalis*
*Pseudomonas aeroginosa*
Enterobactericeae FIG. 7 schematically illustrates a handheld air sampler device 1 according to yet an-other embodiment for surface sampling application in a perspective view.

In this embodiment, the inlet 2 is provided with a surface vacuum nozzle 14 configured for wiping a surface area 15, as explained below. The inlet 2 is formed integral with the surface vacuum nozzle 14. In particular, the inlet 2 as of FIG. 5 may therefore be replaced by the inlet 2 formed integrally with the surface vacuum nozzle 14.

The surface vacuum nozzle 14 comprises a nozzle surface 16 with a plurality of open channels 17. These are arranged and configured to avoid stucking on a surface area 15 when a negative pressure is applied. For example, according to the present embodiment, the channels are arranged (star-like) extending radially from the inlet opening regularly distanced from each other with regular distance angles. The arrangement of the channels, however, is not particularly limited thereto.

The handheld air sampling device 1 is configured for sampling on numerous kinds of surfaces, the surfaces being not particularly restricted, for example:

Rough surfaces
Smooth surfaces
Skin
Clothing
Textile
Complex structures
Organic and inorganic surfaces
Metal
Plastic
Wood
Polymers
Stone In particular the channels 17 at the nozzle surface 16 provide for a pressure compensation allowing wiping the nozzle surface 16 over any kind of surface, in particular those named above, and avoid stucking of the sampling nozzle 14 when negative pressure or vacuum is applied to the outlet 4.

FIG. 8 schematically illustrates a surface area 15 and a wiping pattern.

The wiping pattern as shown by the arrows in FIG. 8 represents a surface sampling with the surface area 15 having the size of 1 $m^2$. This wiping pattern, as an example, has a meander like shape and systematically covers the complete area. However, the wiping pattern is not particularly restricted thereto and may have any other suitable shape.

With an air sampler device 1 as configured in FIGS. 4, 6 and 7, a plurality of applications are possible. Depending on the application, the type of filter element 6 can be chosen from a variety of filter elements. For example, the following types of filters could be used as a filter element in the handhold air sampling device, if cut to a suitable size, which is in the present example a round shape with a diameter of 13 mm, the filter element being not particularly restricted:

Gelatine filter, in particular gelatin membrane filter
Cellulose filter
Nitro cellulose filter
Nylon filter
Nano-Cellulose filter
Polyvinylidine fluoride (PVDF) membrane filter
Polytetrafluoroethylene" (PTFE) membrane filter
Polyethersulfone (PES) filter
Microelectrochemical systems (MEMS) filter
All kind of other filters in a diameter of 13 mm After air sampling, for example two different ways of sample preparation are possible, the sample preparation being not particularly restricted:

Unspecific sample preparation by dissolving the filters, e. g. gelatin filters, after removal from the device and direct processing, e. g. on culturing plates, or in an assay, like PCR, ELISA or other biochemical assay.

Specific sample preparation, e. g. by usage of magnetic beads coated with recombinant antibodies, bacteriophage proteins and/or aptamers to capture specific microorganisms out of the liquid after dissolution of the filters, e. g. gelatin filters.

First experiments with the air sampling arrangement 20 show that the handheld air sampling device 1 has a high efficiency. For example, to capture airborne and surface microorganisms, three in-house measurements were performed with a handheld air sampling device 1 and a gelatine membrane filter, e. g. a gelatine membrane filter as described in WO 99/25465.

The following surfaces were sampled:
1) 1 m² floor surface in a bio-lab with a surface nozzle 14
2) computer keyboard with a surface nozzle 14
3) respiratory sampling the breath of a healthy person with a nozzle 13 configured as mouthpiece The duration of the sampling was one minute and the constant flow rate was 12.5 L/min.

After sampling, gelatin filters were dissolved in water and the solution spread on humid R2A-agar plates. The plates were incubated for 3 days at 20° C., and growth of microorganisms was determined, with the following qualitative results:
1) Predominately bacterial growth was observed to a large extent, so that CFUs (Colony Forming Units) could not be determined.
2) Growth of predominately fungal colonies was observed to a large extent, so that CFUs (Colony Forming Units) could not be determined.
3) Only three CFUs could be observed but the sampling worked.

After these first experiments handheld air sampler device 1 was further tested to capture microorganisms. Different sampling applications were tested again by air sampling arrangement 20 including gelatine membrane filters, as e. g. described in WO 99/25465:
sampling a volume of 1 m³ inside room (indoor) air
sampling of volume of 1 m³ outside (outdoor) air
surface sampling an area of 1 m² of the floor surface
respiratory sampling of several persons
surface sampling of skin from a person's arm
surface sampling of a used computer keyboard Qualitative results of these tests showed a very high capture rate of microorganisms by using the gelatin membrane filters and also by using other filter types.

In addition, gelatin filters were also tested with regard to nucleic acid isolation and detection by polymerase chain reaction (PCR). As a qualitative result, a very low inhibition or dysfunction of the testing was observed.

After sampling, gelatin filters were dissolved in 500 µl water (H2O) and the liquid was put on R2A agar culturing plates. After an incubation duration of 5 days at a temperature of 25° C., different colonies could be observed. This qualitatively demonstrates that enrichment of microorganism on gelatin filters successfully worked.

For example, also the following detection methods could be used after sampling and dissolution of the gelatin filters:
Biological detection after sampling of microorganisms:
Cultivation on culturing plates
Polymerase Chain Reaction (PCR)
Enzyme Linked Immunosorbent Assay (ELISA)
Fluorescence In Situ Hybridization (FISH)
Analytical Profile Index (API)-system
Mass spectroscopy
β-Glucuronidase assay
β-Galactosidase assay Chemical detection after sampling of non-biological particles:
Ion-Mobility Spectrometry (IMS)
Gas Chromatography (GC)
GC-IMS
Raman spectroscopy
Mass spectroscopy
Scanning Electron Microscopy (SEM)
X-ray Photoelectron Spectroscopy (XPS)

FIG. 9A-9C schematically illustrate steps of a method for applying a filter element 6 to a backing element 5 of a handheld air sampling device 1 according to an embodiment.

FIG. 9A shows a holding portion 18 of a handheld air sampler device 1. The holding portion 18 accommodates a backing element 5, which is arranged in the flow channel 3.

In the state shown in FIG. 9A, an airflow through the flow channel 3 is interrupted and the inlet 2 is removed from the holding portion 18.

Furthermore, a section of a top plate 31 of a filter magazine 30 is shown. The top plate 31 comprises a recess 32. Inside the recess 32, a filter receiving step 33 is provided. The filter receiving step 33 is configured for holding a filter element 6, which is stored in the recess 32 in a predefined position.

FIG. 9B shows the holding portion 18 including the backing element 5 inserted into the recess 32 such that the backing element 5 is positioned directly on the filter element 6. The holding portion 18 fits exactly into the recess 32, which has the same dimension as the flange 19 of the inlet 2. Accordingly, the filter element 6 is positioned on the backing element 5 in a predefined position defined by the filter receiving step 33. This position is suitable for the filter element 6 to be sealedly clamped between the sealing element 7 and the backing element 5 once the inlet 2 with its flange 19 is reattached to the holding portion 18.

For holding the filter element 6 on the backing element 5, an airstream through the flow channel 3 is continued.

FIG. 9c shows the holding portion 18 including the backing element 5 and the filter element 6 removed from the recess 32. In this state, the filter element 6 is received on the backing element 5 and held thereon by a pressure difference generated by the airstream through the flow channel 3, as symbolized by an arrow in FIG. 9C. In this way, the filter element 6 stays on the backing element 5 in the predefined position when the backing element 5 is removed from the recess 32.

After removal of the from the recess, the sealing element 7 and the flange 19 of the inlet 2 can be reattached to the holding portion 18 for sealedly clamping the filter element 6 in the flow channel 3. Then, all air passing the flow channel 3 passes the filter element 6.

FIG. 10 schematically illustrates a filter magazine 30 in a sectional perspective view.

The filter magazine 30 comprises a circular top plate 31. The sectional view shows a section through the center 37 of the top plate 31.

The top plate may be configured turnable around a vertical axis (not shown (running through the center 37.

The filter magazine 30 in total comprises eight recesses 32, five of which are depicted in FIG. 10. Of course, the number of recesses 32 is not particularly restricted and can be varied to other numbers, depending on the application.

The recesses 32 are arranged circumferentially in equal distances around the center 37.

The sectional line of the depicted sectional view is running through two of the recesses 32, one shown on the left and one shown the right hand side in FIG. 10. Each recess 32 comprises a filter receiving protrusion or step 33, on which a filter element 6 can be received in a predefined manner, as exemplarily shown in the recess 32 on the left hand side.

Underneath the top plate 31, a sterilizing means 34 configured as a UV lamp is arranged and electrically contacted to a power source (not shown). Furthermore, the bottom of each recess 32 is provided with a UV transmitting window 36. In this way, the filter element 6 stored inside the recess 32 can be sterilized by UV light through the window 36.

Each recess 32 comprises a venting channel 38 entering the recess 32 between the filter receiving protrusion or step 33 and the UV transmitting window 36. In this way, an airflow through the recess 32 is enabled when an airflow in the flow channel 3 of the handheld air sampler device is continued. Such an airflow generates a pressure difference at the filter element 6 stored in the recesses 32 resulting in a force holding the filter element 6 on the backing element 5 when the holding portion 18 is removed from the recess 32, as explained with reference to FIG. 9C.

Figure 7:
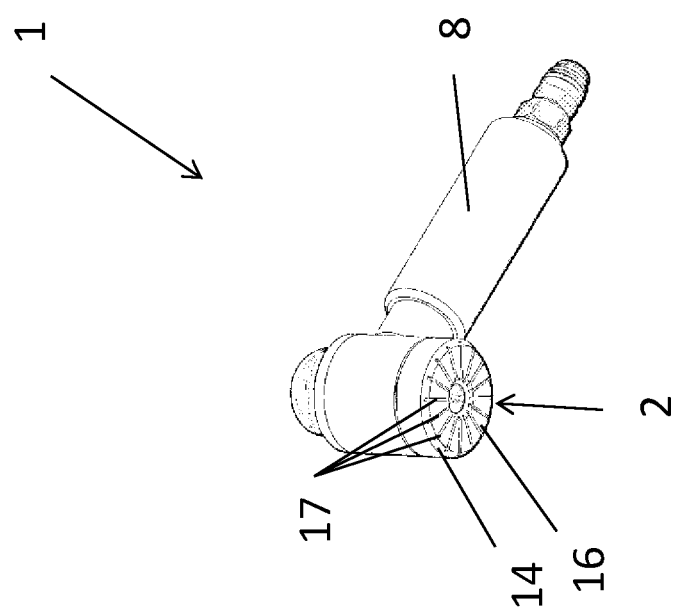
FIG. 7 schematically illustrates a handheld air sampler device according to yet another embodiment for surface sampling application in a perspective view.
Figure 8:
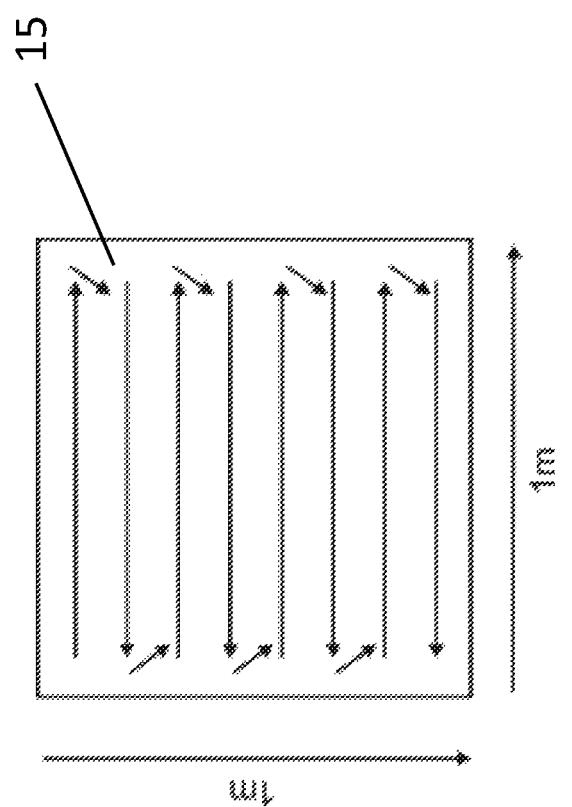
FIG. 8 schematically illustrates a surface area and a wiping pattern.
Figure 11:
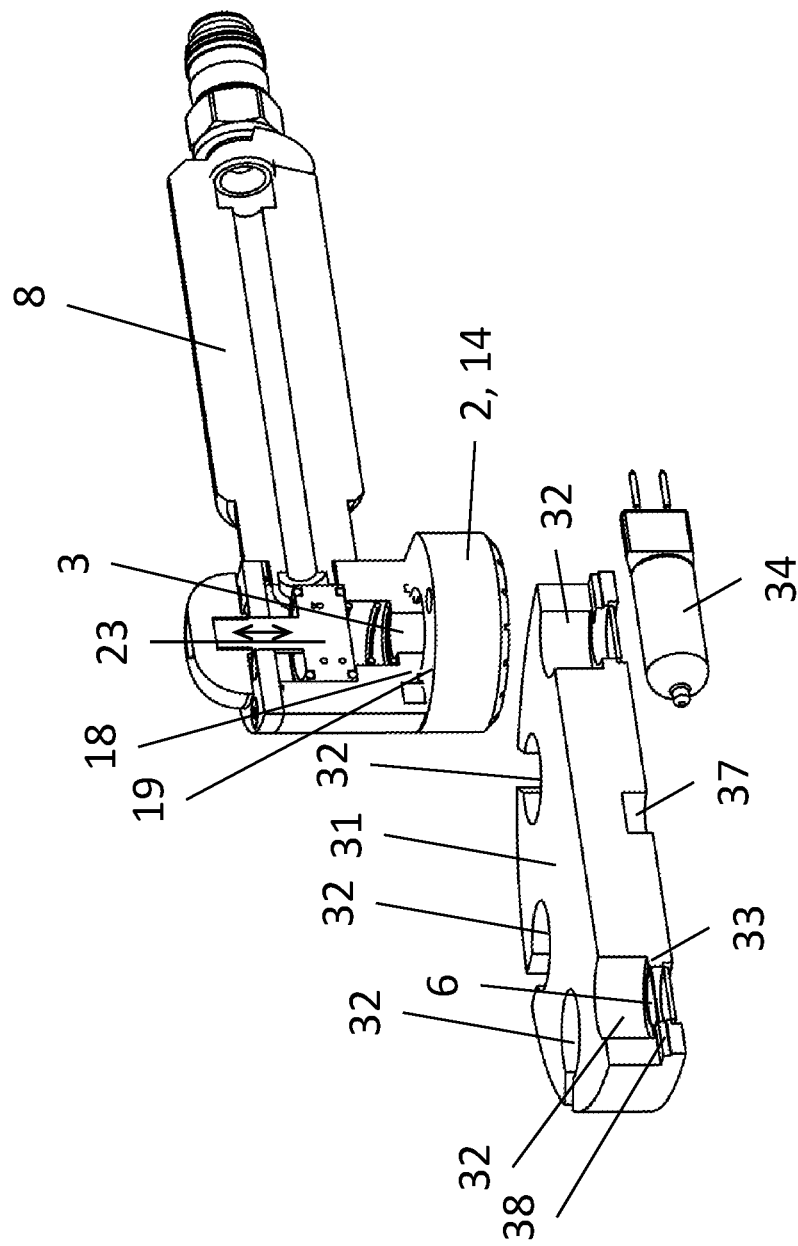
FIG. 11 schematically illustrates a handheld air sampler device according to FIG. 7 and the filter magazine according to FIG. 10 in a sectional perspective view.

FIG. 11 schematically illustrates a handheld air sampler device according to FIG. 7 and the filter magazine according to FIG. 10 in a sectional perspective view.

Here, the inlet 2 is formed integrally with a surface nozzle 14 and attached to the holding portion 18.

The valve 9 is depicted here in a closed state, in which the piston 23 blocks the flow channel 3. Accordingly, the inlet 2 including its flange 19 can be removed from the holding portion 18 in order to pick up or replace a filter element 6. If a used filter element 6 is received on a backing element 5, the used filter element 6 can removed and a new filter element 6 picked up after sterilization.

For sterilizing, the backing element 5 may be inserted into the recess 32 on the right-hand side, in which no filter element is stored. In this way, the backing element 5 is sterilized.

The backing element 5 can then be removed again and the top plate 31 can be turned around its axis such that a recess 32, in which a filter element 6 is stored (such as shown in the recess 32 on the left-hand side) is in alignment with the sterilizing means 34. Accordingly, the filter element 6 is then sterilized and can be picked up after sterilization by inserting the backing element 5 into the respective recess 32, as explained with respect to FIGS. 9A-C.

Figure 12:
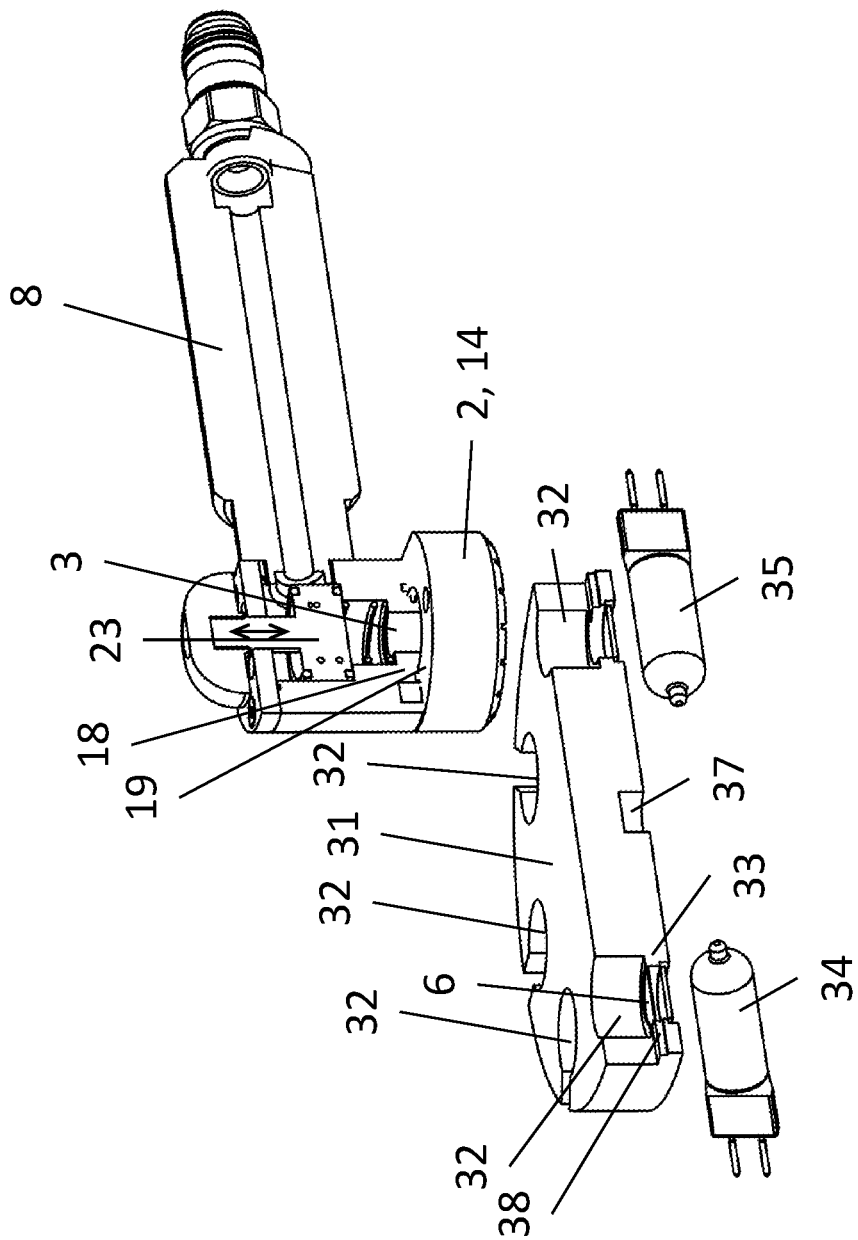
FIG. 12 schematically illustrates a handheld air sampler device according to FIG. 7 and a filter magazine according to another embodiment in a sectional perspective view.

FIG. 12 schematically illustrates a handheld air sampler device 1 according to FIG. 7 and a filter magazine 30 according to another embodiment in a sectional perspective view.

In contrast to the embodiment of FIG. 11, the filter magazine 30 comprises two sterilizing means 34, 35. In contrast to the embodiment, of FIG. 11, a first sterilizing means 34 is here arranged in alignment with the recess 32, in which a filter element 6 is stored, on the left-hand side. On the right hand side, a second sterilizing means 35 is arranged opposed to the first sterilizing means 34 for sterilizing the backing means 5 in the manner as described with respect to FIG. 11.

In this way, the filter element 6 and the backing element 5 can be sterilized at the same time and the filter element 6 can be directly picked up without turning the top plate 31 between the sterilizing steps. Thus, advantageously, for example, a sequence of short sampling cycles can be conducted with a much shorter delay delay.

Although specific embodiments of the invention are illustrated and described herein, it will be appreciated by those of ordinary skill in the art that a variety of alternate and/or equivalent implementations exist. It should be appreciated that the exemplary embodiment or exemplary embodiments are examples only and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that in this document the terms "comprise", "comprising", "include", "including", "contain", "containing", "have", "having", and any variations thereof, are intended to be understood in an inclusive (i.e. non-exclusive) sense, such that the process, method, device, apparatus or system described herein is not limited to those features or parts or elements or steps recited but may include other elements, features, parts or steps not expressly listed or inherent to such process, method, article, or apparatus. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A handheld air sampler device for enrichment of airborne substances or particles, comprising:
    an inlet configured for air intake into a flow channel;
    an outlet configured for fluidically connecting the flow channel to an external vacuum device;
    a permeable backing element arranged in the flow channel, the backing element being configured to receive and support a filter element; and
    a sealing element configured for sealing a filter element received on the backing element such that, when a negative pressure is applied to the outlet, air entering the inlet forms an airstream passing the filter element and airborne substances or particles are enriched in the filter element,
    wherein the air sampler device is configured to be handheld during the enrichment of airborne substances or particles.

2. The handheld air sampler device of claim 1, wherein the device is configured for enrichment of microorganisms, which are enriched in the filter element.

3. The handheld air sampler device of claim 1, wherein at least one of the inlet or the outlet is at least partially formed integrated with or directly connected to a handhold portion.

4. The handheld air sampler device of claim 1, wherein the inlet and the outlet are configured removable from each other for inserting, removing or replacing the filter element.

5. The handheld air sampler device of claim 4, wherein the filter element is configured insertable between the backing element and the sealing element by sealedly clamping the filter element between the backing element and the sealing element such that all air passing the flow channel passes the filter element.

6. The handheld air sampler device of claim 5, further comprising a holding portion at least partially forming the flow channel, wherein the inlet comprises a flange removably attachable to the holding portion with the sealing element therebetween such that the filter element can be sealedly clamped between the backing element and the sealing element when the flange is attached.

7. The handheld air sampler device of claim 1, wherein a valve is arranged in the flow channel for controlling an airflow through the flow channel.

8. The handheld air sampler device of claim 7, wherein the valve comprises an operating element positioned hand operable in use.

9. The handheld air sampler device of claim 8, wherein the operating element is positioned one-handed operable with the same hand the device is handheld with.

10. The handheld air sampler device of claim 1, wherein a flow direction through the inlet is at an angle to a flow direction through the outlet.

11. The handheld air sampler device of claim 1, wherein the inlet is provided with a nozzle configured as mouthpiece for sampling of breath to enrich respiratory microorganisms in the filter element.

12. The handheld air sampler device of claim 1, wherein the inlet is provided with a surface vacuum nozzle configured for wiping a surface area.

13. The handheld air sampler device of claim 12, wherein the surface vacuum nozzle comprises a nozzle surface with a plurality of open channels to avoid stucking on the surface area when a negative pressure is applied.

14. An air sampling arrangement, comprising:
a handheld air sampler device according to claim 1;
a separate vacuum device fluidically connected to the outlet of the handheld air sampler device; and
a filter element received between the backing element and the sealing element of the handheld air sampler device such that a negative pressure applied to the outlet generates an airflow through the inlet which passes the filter element for enrichment of airborne substances or particles.

15. The air sampling arrangement of claim 14, wherein the arrangement is configured for enrichment of microorganisms.

16. A filter magazine for storing and predefined positioning filter elements on a backing element of a handheld air sampler device according to claim 1,
the filter magazine comprising:
a top plate comprising a recess; and
a filter receiving protrusion or step arranged in the recess for holding a filter element in a predefined position such that the filter element can be received on the backing element of the handheld air sampler device in a predefined position by inserting the backing element into the recess.

17. The filter magazine of claim 16, wherein the handheld air sampler device comprises a holding portion at least partially forming the flow channel, wherein the inlet comprises a flange removably attachable to the holding portion with the sealing element therebetween such that the filter element can be sealedly clamped between the backing element and the sealing element when the flange is attached, and wherein the top plate comprises a recess dimensioned equal to the flange of the handheld air sampler device such that the recess fits with the holding portion.

18. The filter magazine of claim 17, wherein the filter element can be received on the backing element of the handheld air sampler device together with the holding portion.

19. The filter magazine of claim 16, wherein the recess is configured as through hole and a first sterilizing means is arranged underneath the top plate for sterilizing a filter element stored in the recess.

20. The filter magazine of claim 19, wherein the first sterilizing means is positionable in alignment with the recess.

21. The filter magazine of claim 19, wherein a plurality of recesses are provided in the top plate.

22. The filter magazine of claim 19, wherein a second sterilizing means is provided underneath the top plate for sterilizing the backing element before a filter is received thereon.

23. The filter magazine of claim 19, wherein the sterilizing means comprises a UV lamp.

24. The filter magazine of claim 23, wherein the UV lamp is arranged underneath a UV transmitting window attached to the top plate.

25. A method for applying a filter element to a backing element of a handheld air sampling device comprising an inlet configured for air intake into a flow channel, an outlet configured for fluidically connecting the flow channel to an external vacuum device, a permeable backing element arranged in the flow channel, the backing element being configured to receive and support a filter element, and
a sealing element configured for sealing a filter element received on the backing element such that, when a negative pressure is applied to the outlet, air entering the inlet forms an airstream passing the filter element and airborne substances or particles are enriched in the filter element,
the method comprising the following steps:
interrupting airflow in the flow channel;
inserting the backing element into a recess of a top plate of a filter magazine with a filter element stored therein, comprising a filter receiving protrusion or step arranged in the recess for holding the filter element in a predefined position such that the filter element can be received on the backing element of the handheld air sampler device in a predefined position by inserting the backing element into the recess; and
continuing airflow in the flow channel such that a pressure difference and a resulting force for holding the filter element on the backing element is generated.

* * * * *